United States Patent [19]

Herzog et al.

[11] 4,066,626

[45] Jan. 3, 1978

[54] LINEAR POLYESTERS BASED ON HETEROCYCLIC DICARBOXYLIC ACIDS

[75] Inventors: Hans Herzog, Badenweiler; Lothar Buxbaum; Thomas Kainmuller, both of Lindenfels, Odenwald, all of Germany; Jürgen Habermeier, Pfeffingen, Switzerland

[73] Assignee: Ciba-Geigy Corporation, Ardsley, N.Y.

[21] Appl. No.: 678,573

[22] Filed: Apr. 20, 1976

[30] Foreign Application Priority Data

Apr. 23, 1975 Switzerland .......................... 5203/75
Feb. 12, 1976 Switzerland .......................... 1707/76

[51] Int. Cl.$^2$ .............................................. C08G 63/68
[52] U.S. Cl. .................................. 260/75 N; 260/47 C
[58] Field of Search ............................ 260/75 N, 47 C

[56] References Cited

U.S. PATENT DOCUMENTS

| 3,856,754 | 12/1974 | Habermeier et al. ............. 260/75 N |
| 3,860,564 | 1/1975 | Habermeier et al. ............. 260/75 N |
| 3,886,123 | 5/1975 | Habermeier et al. ............. 260/75 N |
| 3,994,864 | 11/1976 | Buxbaum et al. ................. 260/75 N |

*Primary Examiner*—Lucille M. Phynes
*Attorney, Agent, or Firm*—Luther A. R. Hall

[57] ABSTRACT

Linear thermoplastic polyesters based on imidazolidine-4,5-dione-dicarboxylic acids are useful moulding compounds with high glass transition temperatures and good working properties.

12 Claims, No Drawings

LINEAR POLYESTERS BASED ON HETEROCYCLIC DICARBOXYLIC ACIDS

The present invention provides linear thermoplastic polyesters based on dicarboxylic acids which contain an imidazolidine-4,5-dione radical, optionally further aromatic and/or aliphatic dicarboxylic acids, alkane diols and/or diols which contain N,N-heterocyclic rings, and a process for their manufacture.

Polyalkylene terephthalates, in particular polyethylene terephthalate, are widely used as engineering plastic materials, because these linear polyesters, after they have been processed by injection moulding or extrusion, yield moulded articles with high mechanical strength properties. However, partly crystalline polyethylene terephthalate moulded articles can only be manufactured by fairly complicated technical means, and the amorphous polyethylene terephthalate, which can be readily processed, has too low a glass transition temperature (Tg) of app. 72° C for many uses. The Tg of partly crystalline polybutylene terephthalate is even only app. 22° C.

There has been no lack of attempts made to modify polyalkylene terephthalates in order to obtain linear polyesters with higher Tg values and improved processing properties. For example, German Offenlegungsschrift No. 2,342,415 postulates the use of hydroxyalkylated 1,1'-methylene-bishydantoins as diol components in the manufacture of linear polyesters based on terephthalic and/or isophthalic acid. German Offenlegungsschrift No. 2,342,431 also proposes the use of hydroxyalkylated benzimidazolones as diol components. Whereas the thus modified polyalkylene terephthalates do possess increased Tg values, the toughness properties of these linear polyesters, for example the impact strength, are nevertheless still not entirely satisfactory.

German Offenlegungsschrift Nos. 2,414,349 and 2,414,287 postulate the use of dicarboxylic acids which contain carboxylic acid groups to increase the Tg. This increase is evidently effected by the formation of hydrogen bridges of the amide groups. However, these copolyesters can absorb too much moisture on account of the NH groups present and this has an adverse effect during storage and processing.

The present invention has for its object the provision of polyesters which have an increased glass transition temperature and improved toughness properties and contain N-substituted acid amide groups.

The present invention accordingly provides linear thermoplastic polyesters with a relative viscosity of 1.2 to 3, measured at 30° C in a 1% solution of equal parts of phenol and tetrachloroethane, and consisting of (a) 5 to 50 molar percent of dicarboxylic acid radicals of the formula I

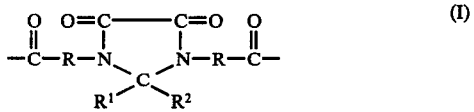

wherein R represents substituted or unsubstituted alkylene containing 1 to 2 carbon atoms in the chain, cyclohexylene, phenylene or benzylene the methylene group of which is attached to the nitrogen atom, and each of $R^1$ and $R^2$ represents hydrogen, alkyl of 1 to 18 carbon atoms, cycloalkyl containing 5 to 8 ring members, phenyl, or $R^1$ and $R^2$ together represent $-(CH_2)_n-$, in which n is 4, 5, 6 or 7, and, if R is phenylene, $R^1$ represents hydrogen and $R^2$ represents alkyl of 1 to 18 carbon atoms or cycloalkyl containing 5 to 8 ring members, b. 0 to 45, preferably 5 to 45 molar percent of terephthalic, isophthalic, 2,6-naphthalenedicarboxylic acid, 4,4'-diphenylsulphone-dicarboxylic acid and/or aliphatic dicarboxylic acid radicals containing 6 to 12 carbon atoms, (c) 50 molar percent of at least one diol radical which is derived from alkylene diols of 2 to 10 carbon atoms, 1,4-cyclohexanediol, 1,4-bis-hydroxymethylcyclohexane, 1,1-methylene-bis-[3-(2'-hydroxyethyl)-5,5-dimethyl hydantoin] and/or a diol of the formula II

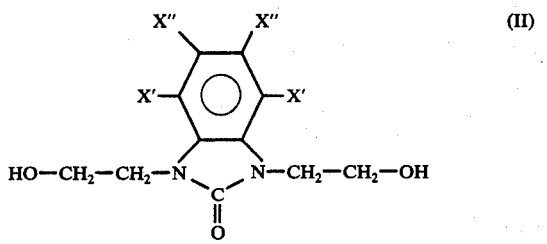

wherein X' and X" represent hydrogen, chlorine or bromine atoms, or X' represents a hydrogen atom and X" represents a chlorine or bromine atom.

The relative viscosity is preferably 1.3 to 2.5. The substituents in the alkylene moiety are preferably alkyl groups containing 1 to 6, in particular 1 or 2, carbon atoms. Examples of R are: methylene, ethylidene, 1,1-propylidene, 2,2-propylidene, 1,1- or 2,2-butylidene, hexylidene, ethylene, 1,2-propylene, 1,2- or 2,3-butylene, 1,2-pentylene, 2,3-hexylene, 1,2- or 3,4-octylene, 5,6-decylene, 7,8-tetradecylene. Methylene, ethylidene, ethylene, phenylene and benzylene are particularly preferred. Of the possible position isomers of cyclohexylene, phenylene and benzylene, the 1,4-derivatives are particularly preferred.

Each of $R^1$ and $R^2$ can be linear or branched alkyl containing preferably 1 to 12, in particular 1 to 6, carbon atoms, and cycloalkyl containing preferably 5 or 6 ring members. In the $-(CH_2)_n$ radical, n is preferably 6 and especially 4 or 5.

Examples of $R^1$ and $R^2$ are: methyl ethyl, propyl, 1-butyl, n-butyl, hexyl, octyl, decyl, dodecyl, tetradecyl, octadecyl. Most preferably each of $R^1$ and $R^2$ is methyl, ethyl or hydrogen.

Preferred additional dicarboxylic acid radicals are terephthalic acid and/or isophthalic acid radicals. Aliphatic dicarboxylic acid radicals of 6 to 12 carbon atoms are for example: adipic acid, pimelic acid, suberic acid, azelaic acid or sebacic acid.

The alkylene diols contain preferably 2 to 6 and in particular 2 to 4 carbon atoms. Examples are: ethylene glycol, 1,2- or 1,3-propanediol, 1,2-, 2,3-, 1,3- or 1,4-butanediol, 1,5-pentanediol, neopentyl glycol, hexamethylene glycol, octanediol, decanediol. It is especially preferred to use ethylene glycol and/or 1,4-butanediol. Particularly preferred diols of component C are the alkylenediols, 1,1-methylene-bis[3-(2'-hydroxyethyl)-5,5-dimethyl hydantoin] and diols of the formula III. In these latter, X' and X" preferably represent hydrogen, chlorine or bromine.

Particularly useful homopolyesters are those consisting of a. 50 molar percent of dicarboxylic acid radicals of the formula I and b. 50 molar percent of 1,4-butanediol or, in particular, ethylene glycol radicals, and copolyesters consisting of a. 5 to 45 molar percent of dicarboxylic acid radicals of the formula I, b. 45 to 5 molar percent of terephthalic acid radicals, c. 35 to 50 molar percent of butanediol radicals or, in particular, ethylene glycol radicals, and d. 0 to 15, preferably 1 to 15, molar percent of radicals of a diol of the formula II.

The polyesters of the present invention are obtained by known processes by polycondensing a. 5 to 50 molar percent of a dicarboxylic acid or polyester-forming derivatives thereof of the formula III

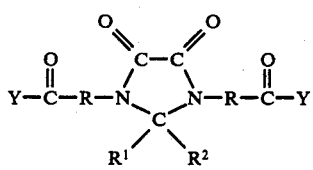

wherein R, R$^1$ and R$^2$ are as defined in formula I and Y represents hydroxyl, methoxy, ethoxy, phenoxy, chlorine or bromine, and b. 0 to 45 molar percent of terephthalic acid, isophthalic acid, 2,6-naphthalenedicarboxylic acid, 4,4'-diphenylsulphone-dicarboxylic acid and/or aliphatic dicarboxylic acids containing 6 to 12 carbon atoms or of the polyester-forming derivatives thereof, with c. 50 molar percent of at least one alkylene diol containing 2 to 10 carbon atoms, 1,4-cyclohexanediol, 1,4-bis-hydroxymethylcyclohexane, 1,1-methylene-bis-[3-(2'-hydroxyethyl(-5,5-dimethyl hydrantoin] and/or a diol of the formula II

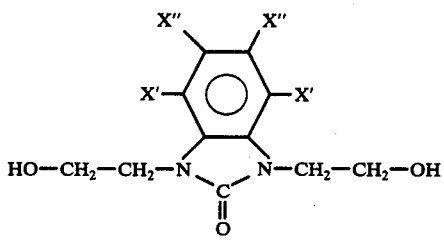

wherein X' and X" represent hydrogen, chlorine or bromine or X' represents hydrogen and X" represents chlorine or bromine, in the presence of catalysts in known manner, to a relative viscosity of 1.2 to 3, measured at 30° C in a 1% solution consisting of equal parts of phenol and tetrachloroethane.

The dicarboxylic acids of the formula III or the polyester-forming derivatives thereof can be obtained by reacting 1 mole of imidazolidine-4,5-diones of the formula

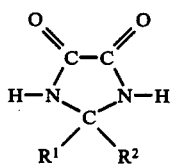

wherein R$^1$ and R$^2$ are as defined in formula III, with 2 moles of a halocarboxylic acid or derivatives thereof of the formula

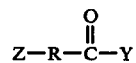

wherein R and Y are as defined in formula III but are not phenylene or chlorine, and Z is chlorine or bromine, with 2 moles of hydrogen chloride or hydrogen bromide being split off, preferably in a polar aprotic solvent, and in the presence of an acid acceptor, for example sodium methylate or sodium ethylate, at elevated temperature, as a rule at 50° to 250° C. The above mentioned imidazolidine-4,5-diones are described in DOS No. 2,018,433, and the halocarboxylic acids are compounds which are known from the literature. The acid dichlorides can be obtained by known processes from the dicarboxylic acids, and the corresponding dicarboxylic acid esters from both by transesterification.

The low molecular dialkyl esters containing 1 to 4 carbon atoms in the molecule, preferably dimethyl and diethyl esters, or the diphenyl esters, are used as polyester-forming derivatives of the dicarboxylic acids (b). The acid dihalides, in particular the acid dichlorides, are also suitable. 1,3-Bis-(4'-methoxycarbonylphenylmethyl)-2,2-dimethyl- imidazolidine-4,5-dione and 1,3-bis-(4'-methoxycarbonyl)-2-methylimidazolidine-4,5-dione are especially preferred.

1,1'-Methylene-bis-[3-(2'-hydroxyethyl)-5,5-dimethyl hydantoin] is a known compound and can be obtained by the process described in U.S. Pat. No. 3,679,681, by adding 2 moles of ethylene oxide to 1 mole of 1,1'-methylene-bis-(5,5-dimethyl hydantoin).

1,3-Di-(2-hydroxyethyl)-benzimidazolone is known from the literature. It can be obtained, for example, by the process described in DOS No. 2,342,432 by addition of 2 moles of ethylene oxide to 1 mole of benzimidazolone. The halogen-substituted benzimidazolone compounds can be obtained by chlorinating and/or brominating 1,3-di-(hydroxyethyl)-benzimidazolone in known manner.

Compounds of the formula II are, for example: 1,3-di-(hydroxyethyl)-benzimidazolone, 1,3-di-(2-hydroxyethyl)-4,5,6,7-tetrachlorobenzimidazolone, 1,3-di-(2-hydroxyethyl)-4,5,6,7-tetrabromobenzimidazolone, 1,3-di-(2-hydroxyethyl)-5,6-dichlorobenzimidazolone and 1,3-di-(2-hydroxyethyl)-5,6-dibromobenzimidazolone.

The compounds of the formula III, in which R is phenylene, R$^1$ is a hydrogen atom and R$^2$ is alkyl or cycloalkyl, can be obtained by the catalytic hydrogenation of the imidazolidines described in Beilstein Pat. No. 24,339, of the formula

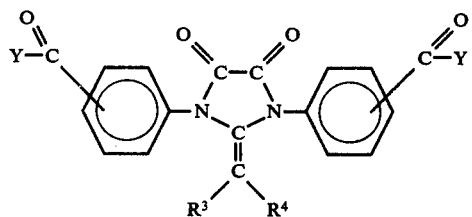

wherein $y$ is as defined in formula III, R$^3$ represents hydrogen and R$^4$ represents alkyl of 1 to 17 carbon atoms, or R$^3$ and R$^4$ together represent alkylene of 4 to 7 carbon atoms.

It is also possible to use mixtures of the diols (c) to obtain the polyesters of the present invention. In doing so, any mixture can be chosen, that is to say the ratio is not critical.

The known processes for obtaining the polyesters of the present invention are, for example, solvent or azeotropic condensation, interface condensation, melt condensation or solid phase condensation, and also combinations of these methods, depending on which polyester-forming derivatives are used.

The polyesters of the present invention can be obtained by esterifying dicarboxylic acids or the polyester-forming derivatives thereof of the formula III and optionally the acids (b), or transesterifying the low molecular dialkyl esters of these dicarboxylic acids, with the aliphatic diols and/or the N,N'-heterocyclicaliphatic diols, in an inert atmosphere, for example in an atmosphere of nitrogen, in the presence of catalysts and while simultaneously removing the water or alkanol that forms, at 150°–250° C, and subsequently carrying out the polycondensation at 200°–270° C and under reduced pressure, in the presence of specific catalysts, until the polycondensation products have the desired viscosity.

When manufacturing polyesters which, in addition to containing the N,N'-heterocyclic-aliphatic diols, also contain aliphatic diols, it is advantageous to use an excess of these diols, so that after the esterifiction or transesterification chiefly monomeric diglycol esters of all dicarboxylic esters are obtained, which are then polycondensed in the presence of a polycondensation catalyst and while distilling off excess aliphatic diol of the formula III in vacuo.

As esterification catalysts it is possible to use, in known manner, amines, inorganic or organic acids, for example hydrochloric acid or p-toluenesulphonic acid, or else metal compounds which are also suitable as transesterification catalysts.

Since some catalysts tend to promote the transesterification and others the polycondensation, it is advantageous to use a combination of several catalysts. Suitable transesterification catalysts are, for example, the oxides, salts or organic compounds of the metals calcium, magnesium, zinc, cadmium, manganese, titanium and cobalt. The metals themselves can also be used as catalysts. The polycondensation is catalysed, for example, by metals like lead, titanium, germanium, tin and, in particular, antimony, or compounds thereof. These catalysts can be added to the reaction mixture together or separately.

The catalysts are used in amounts of approximately 0.001 to 1 percent by weight, referred to the acid component.

In the manufacture of the polyesters of this invention it is particularly advantageous to use those catalysts which promote both the transesterification and the polycondensation. Such catalysts are primarily mixtures of different metals or metal compounds as well as corresponding metal alloys.

The polycondensation reaction is carried out until the polyesters have a relative viscosity of 1.2 to 3, preferably 1.3 to 2.5. Depending on the nature of the catalyst used and on the size of the batch, the reaction times are from about 30 minutes to several hours. After the resultant polyester melt has been removed from the reaction vesel and cooled, it is granulated or shredded in the usual way.

The polycondensation can also be carried out in such a manner that the starting compounds are initially condensed in the melt to a certain viscosity. Then the precondensate obtained is granulated, for example using an underwater granulator, and the granulate is dried and then subjected to a solid phase condensation in vacuo and at a temperature below the melting point of the granulate. Higher viscosities of the polyesters can thereby be attained.

Another process for obtaining the homopolyesters and copolyesters of the present invention consists in polycondensing dicarboxylic acid dihalides of the formula III and dicarboxylic acid dihalides of the dicarboxylic acids (b), preferably the corresponding acid chlorides, with the aliphatic diols and/or the N,N'-heterocyclicaliphatic diols, in the presence of a basic catalyst and in the temperature range from 0° to 180° C, with attendant dehydrohalogenation.

Preferably amines or quaternary ammonium salts are used as basic catalysts. The amount of baic catalyst can be from 0.1 to 100 molar percent, referred to the acid halides. This process can also be carried out with or without a solvent.

In the working up of the polyester melt or before the polymerisaticn reaction, it is possible to add to the reaction mass inert additives of all kinds, for example reinforcing fillers, in particular 5 to 20 percent by weight of sized glass fibres, inorganic or organic pigments, fluorescent brighteners, matting agents, crystallisation promoters, and flameproofing agents, for example antimony trioxide and organic compounds with a high content of chlorine and bromine.

If the polymerisation is carried out batchwise, the inert additives can be added during the final condensation steps, for example in the solid phase condensation or also at the conclusion of the melt condensation.

The polyesters of the present invention can be partly crystalline or amorphous, depending on which dicarboxylic acids and which diols are used as starting components and in what ratios they are used. Compared with polyalkylene terephthalates they have a higher glass transition temperature, and compared with similar polyesters and copolymers they have improved toughness properties. A further distinguishing feature is that they absorb less moisture.

The polyesters of this invention are colourless to yellow in colour and constitute thermoplastic materials from which it is possible to obtain moulded articles with useful thermomechanical properties by the customary moulding processes, for example casting, injection moulding and extruding. The polyesters can be readily processed in conventional injection moulding machines.

The polyesters of the present invention are particularly suitable for use as engineering plastic materials which can be used for obtaining moulded articles, such as gear wheels, containers for chemicals or foodstuffs, machine and apparatus parts, sheets, boards, films, thermoplastic adhesives, coatings, and also for making semi-finished products which can be machined. The polyesters can also be used for coating objects, for example by the known powder coating methods.

The polyesters obtained in the following Examples are more closely characterised by the following characteristic data:

The polyesters are characterised by those morphological changes which are measured by differential thermoanalysis from a sample which has been tempered for 3 minutes at 30° C above the melting or softening point and then rapidly chilled. The chilled sample is heated by means of a Perkin-Elmer "DSC-2B" differential scanning calorimeter with a heating speed of 16° C/min. The critical moment in the sudden increase of the specific heat in the thermogram indicates the glass transition temperature, the tip of the exothermic peak indicates the crystallisation temperature, and the tip of the endothermic peak indicates the melt temperature. Where a Tg range is indicated, for example Tg = 160°–170° C, this means the range in which the specific heat in the thermogram increases rapidly. The relative viscosity of the polycondensates of the Examples is measured in solutions of 1 g of polyester in 100 ml of a mixture consisting of equal parts of phenol and tetrachloroethane at 30° C. The softening temperature is determined on a Kofler heating table microscope with a heating speed of 15° C/min., the procedure being that a cross is formed from two threads and the softening temperature is indicated as that temperature at which the sharp angles of the cross disappear. The nitrogen content is determined by elemental analysis.

A. MANUFACTURE OF THE STARTING MATERIALS

Example 1

1,3-bis-(4'-methoxycarbonylphenylmethyl)-2,2-dimethylimidazolidine-4,5-dione

In a 4-necked flask, equipped with stirrer, reflux cooler, thermometer and drip funnel, a solution of 110.8 g (0.6 mole) of p-chloromethylbenzoic acid methyl ester in 150 ml of hexamethylphosphoric triamide is added dropwise, with stirring, at 25° C to a solution (prepared at 5°–10° C) of 38.4 g (0.3 mole) of 2,2-dimethylimidazolidine-4,5-dione and 32.4 g (0.6 mole) of sodium methylate in 225 ml of anhydrous methanol and 225 ml of hexamethylphosphoric triamide.

When the addition is complete, the mixture is stirred for 2 hours at 80° C. After it has cooled to room temperature, the resultant brown suspension is poured, with vigorous stirring, into app. 2000 ml of ice water. The crystalline precipitate which has formed is filtered off after 1 hour, washed thoroughly with water and suction dried.

The crude product is recrystallised from 3000 ml of n-butanol and dried in vacuo (1 Torr) for 8 hours at 100° C. Yield 38.4 g of a colourless crystalline product with a melting point of 242°–245° C.

The infra-red and nuclear magnetic resonance spectra of the compound confirm the presumed structure.

B. MANUFACTURING EXAMPLES

Example 2

Copolyester of ethylene glycol and dimethyl terephthalate 4.52 g of dimethyl terephthalate, 4.54 g of ethylene glycol and 4.24 g (30 molar %) of 1,3-bis-(4'-methoxycarbonylphenylmethyl)-2,2-dimethylimidazolidine-4,5-dione are put into a 200 ml glass reactor equipped with stirrer, nitrogen inlet and cooler, then 0.01% of zinc (as acetate) and 0.04% of germanium (as butylate) are added. The reaction mixture is heated under nitrogen in an oil bath to 250° C in the course of 1 hour and kept for a further half-hour at this temperature. During this time 98% of the theoretical amount of methanol is distilled off.

The temperature of the oil bath is then adjusted to 260° C and a vacuum of 0.2 Torr is simultaneously applied. When this vacuum is attained, condensation is carried out with stirring for 50 minutes. Then nitrogen is introduced and the polyester is removed from the reactor. The relative viscosity of this copolyester is 1.78 and the glass transition temperature is 104° C.

Example 3

Homopolyester of ethylene glycol 4.24 g of 1,3-bis-(4'-methoxycarbonylphenylmethyl)-2,2-dimethylimidazolidine-4,5-dione and 4.5 g of ethylene glycol are put into a 200 ml glass reactor equipped with stirrer, nitrogen inlet and cooler, and 0.01% of zinc (as acetate) and 0.03% of antimony (as antimony trioxide) are added thereto. The reaction mixture is heated in an oil bath to 200° C in the course of 40 minutes, then the temperature is raised to 240° C and kept thereat for 80 minutes. During this time 99% of the theoretical amount of methanol distills off.

The temperature of the oil bath is then adjusted to 260° C and after half an hour a vacuum of 0.05 Torr is carefully applied. After this vacuum has been attained, polycondensation is effected for 20 minutes with stirring, then nitrogen is introduced and the polyester is removed from the reactor. The relative viscosity of the homopolyester is 1.87 and the glass transition temperature is 145° C.

Examples 4–11

A number of other polyesters are manufactured in a manner analogous to that described in Example 2:

| Ex. | Composition | Molar % | rel. viscosity | $T_E$ (° C) | $T_G$ (° C) |
|---|---|---|---|---|---|
| 4 | DMT + BD + B | 0.4:0.1:0.5 | 1.93 | 182+ | 56 |
| 5 | DMT + BD + EG | 0.1:0.4:0.5 | 1.62 | 215 | 166 |
| 6 | DMT + BD + B Cl + | 0.05:0.45:0.35:0.15 | 1.66 | 165 | 91 |
| 7 | DMT + BM + EG | 0.35:0.15:0.5 | 1.43 | 175 | 122 |
| 8 | BM + B | 0.5:0.5 | n.l. | 320+ | 120 |
| 9 | DMT + BP + EG | 0.35:0.15:0.5 | 1.80 | 185 | 122 |
| 10 | DMT + BD + B + M | 0.05:0.45:0.15 | 1.58 | 170 | 95 |
| 11 | DMT + DMI + BD + B | 0.2:0.1:0.2:0.5 | 1.73 | 140 | 65 |

BD: 1,3-bis-(4'-methoxycarbonylphenylmethyl)-2,2-dimethylimidazolidine-4,5-dione
BM: 1,3-bis-(4'-methoxycarbonylphenyl)-2-methyl-imidazolidine-4,5-dione
BP: 1,3-bis-(4'-methoxycarbonylphenylmethyl)-2,2-pentamethylenimidazolidine-4,5-dione
Cl: N,N'-bis-(2-hydroxyethyl)-4,5,6,7-tetrachloro-benzimidazolone
M: 1,1-methylene-bis-[3-(2'-hydroxyethyl)-5,5-dimethyl hydantoin]
DMT: dimethyl terephthalate
EG: ethylene glycol
B: butanediol-1,4

We claim:

1. A linear thermoplastic polyester with a relative viscosity of 1.2 to 3, measured at 30° C in a 1% solution in a solvent consisting of equal parts of phenol and tetrachloroethane, and having a structural formula consisting of 50 molar percent of radicals derived from the dicarboxylic acids of components (a) plus (b) and 50 molar percent of radicals derived from the diols of component (c), which consists essentially of
   a. 5 to 50 molar percent of dicarboxylic acid radicals of formula I

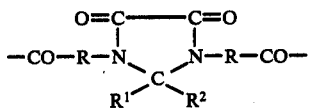

wherein R represents alkylene of 1 to 2 carbon atoms; alkylene of 1 to 2 carbon atoms substituted with alkyl of 1 to 6 carbon atoms; cyclohexylene, phenylene or benzylene, the methylene group of which is attached to the nitrogen atom; and each of $R^1$ and $R^2$ represents hydrogen, alkyl of 1 to 18 carbon atoms, cycloalkyl of 5 to 5 ring members or phenyl; or $R^1$ and $R^2$ together represent $-(CH_2)_n-$, in which $n$ is 4, 5, 6 or 7, and if R is phenylene, $R^1$ represents hydrogen and $R^2$ represents alkyl of 1 to 18 carbon atoms or cycloalkyl of 5 to 8 ring members;

b. 0 to 45 molar percent of dicarboxylic acid radicals derived from the acids selected from the group consisting of terephthalic acid, isophthalic acid, 2,6-naphthalenedicarboxylic acid, 4,4'-diphenylsulfone-dicarboxylic acid and alkanedioic acids of 6 to 12 carbon atoms; and c. 50 molar percent diol radicals of at least one diol derived from the diols selected from the group consisting of the alkylene diols of 2 to 10 carbon atoms; 1,4-cyclohexanediol, 1,4-bis-(hydroxymethyl)cyclohexane, 1,1'-methylene-bis [3-(2-hydroxyethyl)-5,5-dimethylhydantoin] and a diol of the formula II

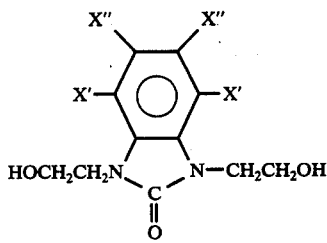

wherein X' and X" represent hydrogen, chlorine or bromine, or X' represents hydrogen and X" represents chlorine or bromine.

2. A polyester according to claim 1, wherein R represents methylene, ethylidene, ethylene, 1,4-phenylene or 1,4-benzylene.

3. A polyester according to claim 1, wherein R represents 1,4-benzylene and $R^1$ and $R^2$ represent methyl.

4. A polyester according to claim 1 which contains 5 to 45 molar percent of component (b).

5. A polyester according to claim 1 wherein $R^1$ and $R^2$ are alkyl of 1 to 6 carbon atoms.

6. A polyester according to claim 1 which contains as component (b) acid radicals derived from the acids selected from the group consisting of terephthalic acid and isophthalic acid.

7. A polyester according to claim 1 which contains as component (c) diol radicals derived from the diols selected from the group consisting of the alkylene diols of 2 to 6 carbon atoms.

8. A polyester according to claim 7 wherein the alkylene diol is selected from the group consisting of ethylene glycol and 1,4-butanediol.

9. A polyester according to claim 1 which contains
   a. 50 molar percent of dicarboxylic acid radicals of formula I, and
   c. 50 molar percent of diol radicals of 1,4-butanediol.

10. A polyester according to claim 1 which contains
    a. 50 molar percent of dicarboxylic acid radicals of formula I, and
    c. 50 molar percent of diol radicals of ethylene glycol.

11. A polyester according to claim 1 which contains
    a. 5 to 45 molar percent of dicarboxylic acid radicals of formula I,
    b. 45 to 5 molar percent of the radicals derived from terephthalic acid, and
    c. 35 to 50 molar percent of diol radicals of 1,4-butanediol and 0 to 15 molar percent of diol radicals of a diol of formula II.

12. A polyester according to claim 1 which contains
    a. 5 to 45 molar percent of dicarboxylic acid radicals of formula I.
    b. 45 to 5 molar percent of the radicals derived from terephthalic acid, and
    c. 35 to 50 molar percent of diol radicals of ethylene glycol and 0 to 15 molar percent of diol radicals of a diol of formula II.

* * * * *